United States Patent [19]

Heinemann et al.

[11] Patent Number: 5,385,905
[45] Date of Patent: Jan. 31, 1995

[54] SUBSTITUTED PYRIDYLPYRIMIDINES

[75] Inventors: Ulrich Heinemann, Leichlingen; Thomas Himmler, Odenthal; Stefan Dutzmann, Hilden; Gerd Hänbler, Leverkusen; Heinz-Wilhelm Dehne, Monheim, all of Germany

[73] Assignee: Bayer Aktiengesellschaft, Leverkusen, Germany

[21] Appl. No.: 19,989

[22] Filed: Feb. 18, 1993

[30] Foreign Application Priority Data

Feb. 28, 1992 [DE] Germany .............................. 4206148

[51] Int. Cl.⁶ ..................... C07D 401/04; A01N 43/54
[52] U.S. Cl. ....................................... 514/256; 544/333
[58] Field of Search .......................... 514/256; 544/333

[56] References Cited

U.S. PATENT DOCUMENTS

| | | | |
|---|---|---|---|
| 5,022,915 | 6/1991 | Prisbylla | 544/333 |
| 5,185,339 | 2/1993 | Pilkington et al. | 544/333 |
| 5,208,239 | 5/1993 | Robson et al. | 544/333 |

FOREIGN PATENT DOCUMENTS 0407899  1/1991  European Pat. Off. .
1271116  5/1965  Germany .

*Primary Examiner*—John M. Ford
*Attorney, Agent, or Firm*—Sprung Horn Kramer & Woods

[57] ABSTRACT

New substituted pyridylpyrimidines of the formula (I)

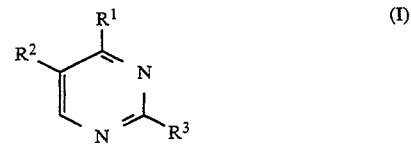

in which
R¹, R² and R³ have the meaning given in the description, their preparation, and their use for combating pests.

Formula (I) provides a general definition for the new compounds. They can be prepared by analogous processes, for example from suitable pyridylamidine hydrochlorides with suitable enamino ketones.

8 Claims, No Drawings

SUBSTITUTED PYRIDYLPYRIMIDINES

The invention relates to new substituted pyridylpyrimidines, to a process for their preparation, and to their use as pesticides.

It has been disclosed that certain substituted pyridylpyrimidines such as, for example, the compound 2-(2-pyridyl)-4-n-propylamino-6-phenyl-pyrimidine have fungicidal properties (compare, for example, EP 407 899).

However, the activity of these previously known compounds is not entirely satisfactory in all fields of application, in particular when low amounts and concentrations are applied.

New substituted pyridylpyrimidines of the general formula (I)

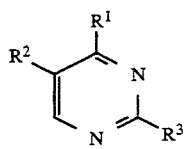

in which
$R^1$ represents alkyl, halogenoalkyl or optionally substituted cycloalkyl,
$R^2$ represents optionally substituted phenyl and
$R^3$ represents optionally substituted pyridyl, have been found.

Furthermore, it has been found that the new substituted pyridylpyrimidines of the general formula (I)

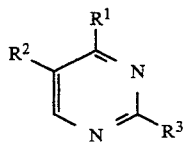

in which
$R^1$ represents alkyl, halogenoalkyl or optionally substituted cycloalkyl,
$R^2$ represents optionally substituted phenyl and
$R^3$ represents optionally substituted pyridyl, are obtained when pyridylamidine hydrochlorides of the formula (II)

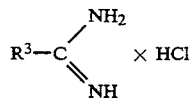

in which
$R^3$ has the abovementioned meaning, are reacted with enamino ketones of the formula (III)

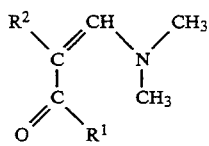

in which $R^1$ and $R^2$ have the abovementioned meaning, if appropriate in the presence of a diluent and if appropriate in the presence of a reaction auxiliary.

Finally, it has been found that the new substituted pyridylpyrimidines of the general formula (I) have a good fungicidal activity.

Surprisingly, the substituted pyridylpyrimidines of the general formula (I) according to the invention show a markedly better fungicidal activity than the substituted pyridylpyrimidines which are known from the prior art such as, for example, the compound 2-(2-pyridyl)-4-n-propylamino-6-phenyl-pyrimidine, which are similar compounds chemically and from the point of view of their action.

Formula (I) provides a general definition of the substituted pyridylpyrimidines according to the invention. Preferred compounds of the formula (I) are those in which $R^1$ represents straight-chain or branched alkyl having 1 to 6 carbon atoms, straight-chain or branched halogenoalkyl having 1 to 6 carbon atoms and 1 to 13 identical or different halogen atoms, or represents cycloalkyl which has 3 to 7 carbon atoms and which is monosubstituted or polysubstituted by identical or different substituents, suitable substituents in each case being:

halogen, straight-chain or branched alkyl having 1 to 6 carbon atoms or straight-chain or branched halogenoalkyl having 1 to 6 carbon atoms and 1 to 13 identical or different halogen atoms, $R^2$ represents phenyl which is optionally monosubstituted or polysubstituted by identical or different substituents, suitable substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms, and represents 2-pyridyl, 3-pyridyl or 4-pyridyl, each of which is monosubstituted or polysubstituted by identical or different substituents, suitable substituents in each case being those mentioned in the case of $R^2$.

Particularly preferred compounds of the formula (I) are those in which $R^1$ represents straight-chain or branched alkyl having 1 to 4 carbon atoms, straight-chain or branched halogenoalkyl having 1 to 4 carbon atoms and 1 to 9 identical or different halogen atoms, or represents cycloalkyl which has 3 to 6 carbon atoms and which is optionally monosubstituted to tetrasubstituted by identical or different substituents, suitable substituents being:

halogen, straight-chain or branched alkyl having 1 to 4 carbon atoms or straight-chain or branched halogenoalkyl having 1 to 4 carbon atoms and 1 to 9 identical or different halogen atoms, R[2] represents phenyl which is optionally monosubstituted to pentasubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl, and R[3] represents 2-pyridyl or 4-pyridyl, each of which is optionally monosubstituted to tetrasubstituted by identical or different substituents, suitable substituents in each case being those mentioned in the case of R[2].

Very particularly preferred compounds of the formula (I) are those in which

R[1] methyl, ethyl, n- or i-propyl, n-, i-, s- or t-butyl, represents straight-chain or branched halogenoalkyl having 1 to 4 carbon atoms and 1 to 5 identical or different halogen atoms - in particular fluorine or chlorine - or represents cyclopropyl, cyclobutyl, cyclopentyl or cyclohexyl, each of which is optionally monosubstituted or disubstituted by identical or different substituents, suitable cycloalkyl substituents in each case being:

fluorine, chlorine, bromine, methyl, ethyl, n- or i-propyl, chloromethyl or trifluoromethyl, R[2] represents phenyl which is optionally monosubstituted to trisubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio and R[3] represents 2-pyridyl which is optionally monosubstituted or disubstituted by identical or different substituents, suitable substituents in each case being those mentioned in the case of R[2].

Individual compounds which may be mentioned in addition to those mentioned in the Preparation Examples are the following substituted pyridylpyrimidines of the general formula (I):

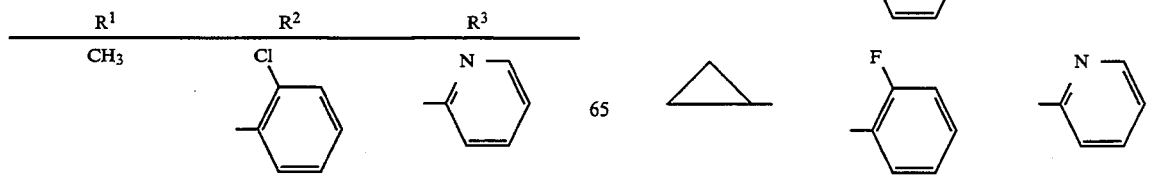

-continued $$\underset{\underset{N}{\parallel}}{\overset{R^1}{\underset{R^2}{\bigvee}}}\overset{N}{\underset{R^3}{\parallel}} \quad (I)$$

| R¹ | R² | R³ |
|---|---|---|
| cyclopropyl-C(Cl)- | 2-F-phenyl | 2-pyridyl |
| cyclopropyl-C(F)- | 2-F-phenyl | 2-pyridyl |
| cyclopropyl-C(CH₃)- | 2-F-phenyl | 2-pyridyl |
| cyclohexyl-H | 2-F-phenyl | 2-pyridyl |
| (CH₃)₂CF- | 2-F-phenyl | 2-pyridyl |
| (CH₃)₂CCl- | 2-F-phenyl | 2-pyridyl |
| (CH₃)₂C(CH₂F)- | 2-F-phenyl | 2-pyridyl |
| (CH₃)₂C(CH₂Cl)- | 2-F-phenyl | 2-pyridyl |
| (ClCH₂)₂C(CH₃)- | 2-F-phenyl | 2-pyridyl |
| n-C₃H₇ | 2-F-phenyl | 2-pyridyl |

-continued $$\underset{\underset{N}{\parallel}}{\overset{R^1}{\underset{R^2}{\bigvee}}}\overset{N}{\underset{R^3}{\parallel}} \quad (I)$$

| R¹ | R² | R³ |
|---|---|---|
| t-C₄H₉ | 2-F-phenyl | 2-pyridyl |
| t-C₄H₉ | 4-Cl-phenyl | 2-pyridyl |
| C₂H₅ | 4-Cl-phenyl | 2-pyridyl |
| CH₃ | 4-Cl-phenyl | 2-pyridyl |
| cyclopropyl-C(Cl)- | 4-Cl-phenyl | 2-pyridyl |
| cyclopropyl-C(F)- | 4-Cl-phenyl | 2-pyridyl |
| cyclopropyl-C(CH₃)- | 4-Cl-phenyl | 2-pyridyl |
| (CH₃)₂CF- | 4-Cl-phenyl | 2-pyridyl |
| (CH₃)₂CCl- | 4-Cl-phenyl | 2-pyridyl |
| (CH₃)₂C(CH₂F)- | 4-Cl-phenyl | 2-pyridyl |
| (CH₃)₂C(CH₂Cl)- | 4-Cl-phenyl | 2-pyridyl |
| (ClCH₂)₂C(CH₃)- | 4-Cl-phenyl | 2-pyridyl |

-continued $$\underset{R^2}{\overset{R^1}{\underset{N}{\bigvee}}}\underset{R^3}{\overset{N}{\bigvee}} \quad (I)$$

| R¹ | R² | R³ |
|---|---|---|
| 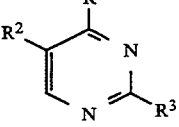 (F-CH₂-C(CH₃)(CH₂F)-) | 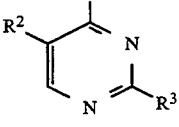 (4-Cl-phenyl) | 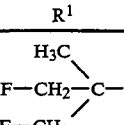 (2-pyridyl) |
| t-C₄H₉ | 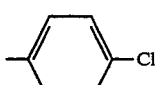 (4-F-phenyl) | 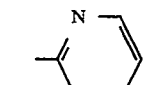 (2-pyridyl) |
| n-C₃H₇ | 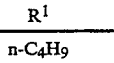 (4-F-phenyl) | 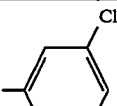 (2-pyridyl) |
| C₂H₅ | 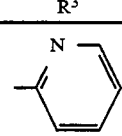 (4-F-phenyl) |  (2-pyridyl) |
| CH₃ | 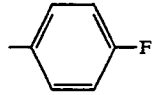 (4-F-phenyl) | 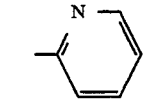 (2-pyridyl) |
| 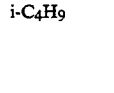 (cyclopropyl-CH(CH₃)-) | 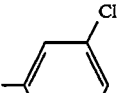 (4-F-phenyl) | 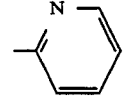 (2-pyridyl) |
|  (cyclopentyl) | 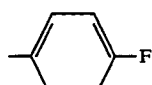 (4-F-phenyl) | 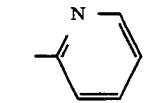 (2-pyridyl) |
| 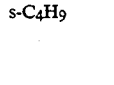 ((CH₃)₂CF-) | 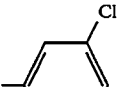 (4-F-phenyl) | 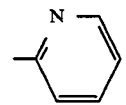 (2-pyridyl) |
|  (F-CH₂-C(CH₃)₂-) | 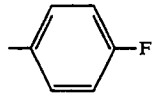 (4-F-phenyl) | 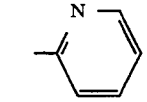 (2-pyridyl) |
| n-C₃H₇ | 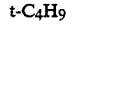 (3-Cl-phenyl) | 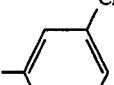 (2-pyridyl) |
| i-C₃H₇ | 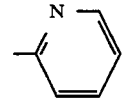 (3-Cl-phenyl) |  (2-pyridyl) |
| n-C₄H₉ | 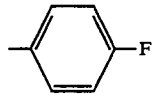 (3-Cl-phenyl) | 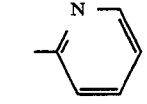 (2-pyridyl) |
| i-C₄H₉ |  (3-Cl-phenyl) | 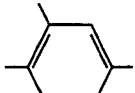 (2-pyridyl) |
| s-C₄H₉ | 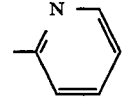 (3-Cl-phenyl) | 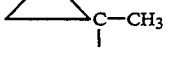 (2-pyridyl) |
| t-C₄H₉ | 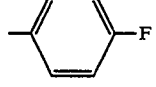 (3-Cl-phenyl) | 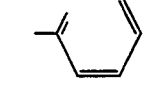 (2-pyridyl) |
| C₂H₅ | 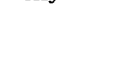 (2,4-diCl-phenyl) | 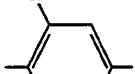 (2-pyridyl) |
| CH₃ | 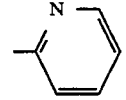 (2,4-diCl-phenyl) |  (2-pyridyl) |
| 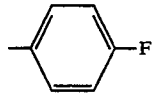 (cyclopropyl) | 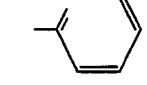 (2,4-diCl-phenyl) | 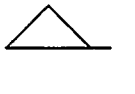 (2-pyridyl) |
| n-C₃H₇ | 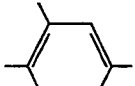 (2,4-diCl-phenyl) | 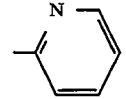 (2-pyridyl) |
| n-C₄H₉ | 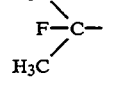 (2,4-diCl-phenyl) |  (2-pyridyl) |
| i-C₄H₉ | 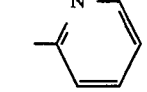 (2,4-diCl-phenyl) | 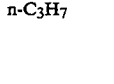 (2-pyridyl) |

-continued $$\text{(I)}$$

| R¹ | R² | R³ |
|---|---|---|
| s-C₄H₉ | 2,4-di-Cl-phenyl | 2-pyridyl |
| t-C₄H₉ | 2,4-di-Cl-phenyl | 2-pyridyl |
| C₂H₅ | 2,4-di-F-phenyl | 2-pyridyl |
| CH₃ | 2,4-di-F-phenyl | 2-pyridyl |
| cyclopropyl | 2,4-di-F-phenyl | 2-pyridyl |
| 1-chlorocyclopropyl | 2,4-di-F-phenyl | 2-pyridyl |
| 1-fluorocyclopropyl | 2,4-di-F-phenyl | 2-pyridyl |
| 1-methylcyclopropyl | 2,4-di-F-phenyl | 2-pyridyl |
| cyclohexyl | 2,4-di-F-phenyl | 2-pyridyl |
| (CH₃)₂CCl- | 2,4-di-Cl-phenyl | 2-pyridyl |

-continued $$\text{(I)}$$

| R¹ | R² | R³ |
|---|---|---|
| (CH₃)₂C(CH₂F)- | 2,4-di-Cl-phenyl | 2-pyridyl |
| (CH₃)₂C(CH₂Cl)- | 2,4-di-F-phenyl | 2-pyridyl |
| n-C₃H₇ | 2,4-di-F-phenyl | 2-pyridyl |
| i-C₃H₇ | 2,4-di-F-phenyl | 2-pyridyl |
| n-C₄H₉ | 2,4-di-Cl-phenyl | 2-pyridyl |
| i-C₄H₉ | 2,4-di-F-phenyl | 2-pyridyl |
| s-C₄H₉ | 2,4-di-F-phenyl | 2-pyridyl |
| t-C₄H₉ | 2,4-di-F-phenyl | 2-pyridyl |
| C₂H₅ | 2-Cl-phenyl | 4-methyl-2-pyridyl |
| CH₃ | 2-Cl-phenyl | 4-methyl-2-pyridyl |

-continued
$$\begin{array}{c} R^2 \diagdown \underset{\underset{R^3}{\overset{N}{\bigvee}}}{\overset{R^1}{\bigvee}} \end{array} \quad (I)$$
| R¹ | R² | R³ |
|---|---|---|
| 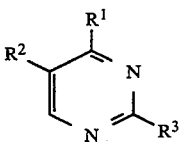 | 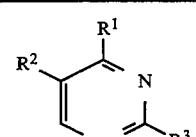 | 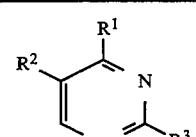 |
| 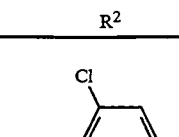 | 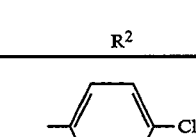 | 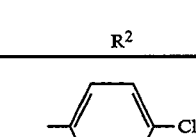 |
| 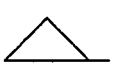 |  |  |
| 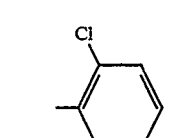 | 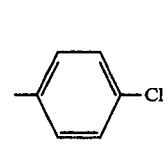 | 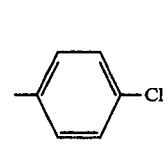 |
| 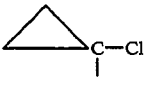 | 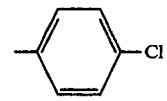 | 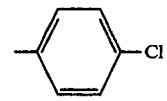 |
| 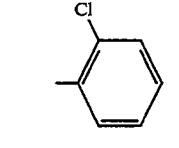 | 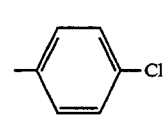 | 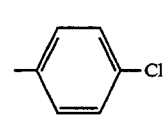 |
| 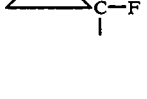 | 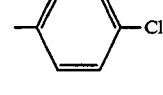 | 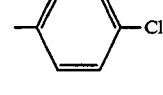 |
| 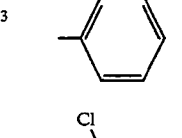 | 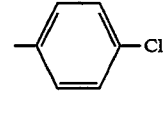 | 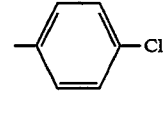 |
| 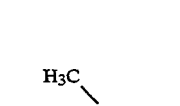 | 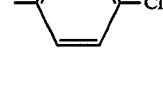 | 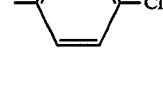 |
| 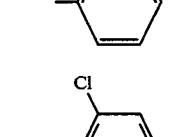 | 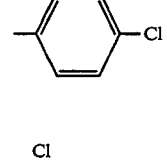 | 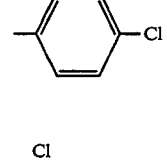 |
-continued
$$\begin{array}{c} R^2 \diagdown \underset{\underset{R^3}{\overset{N}{\bigvee}}}{\overset{R^1}{\bigvee}} \end{array} \quad (I)$$
| R¹ | R² | R³ |
|---|---|---|
| n-C₃H₇ | 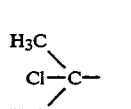 | 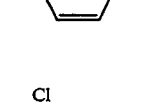 |
| i-C₃H₇ | 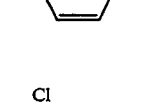 | 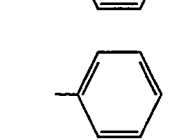 |
| n-C₄H₉ | 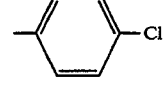 | 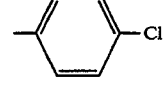 |
| i-C₄H₉ | 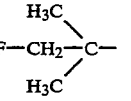 | 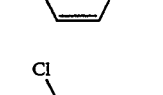 |
| s-C₄H₉ | 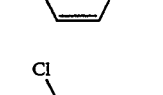 | 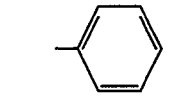 |
| t-C₄H₉ | 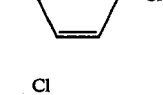 | 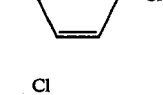 |
| CH₃ | 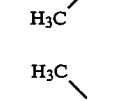 | 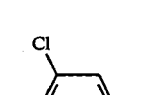 |
| C₂H₅ | 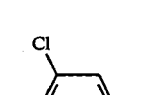 |  |
| 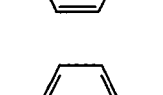 | 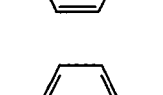 | 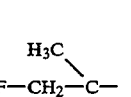 |

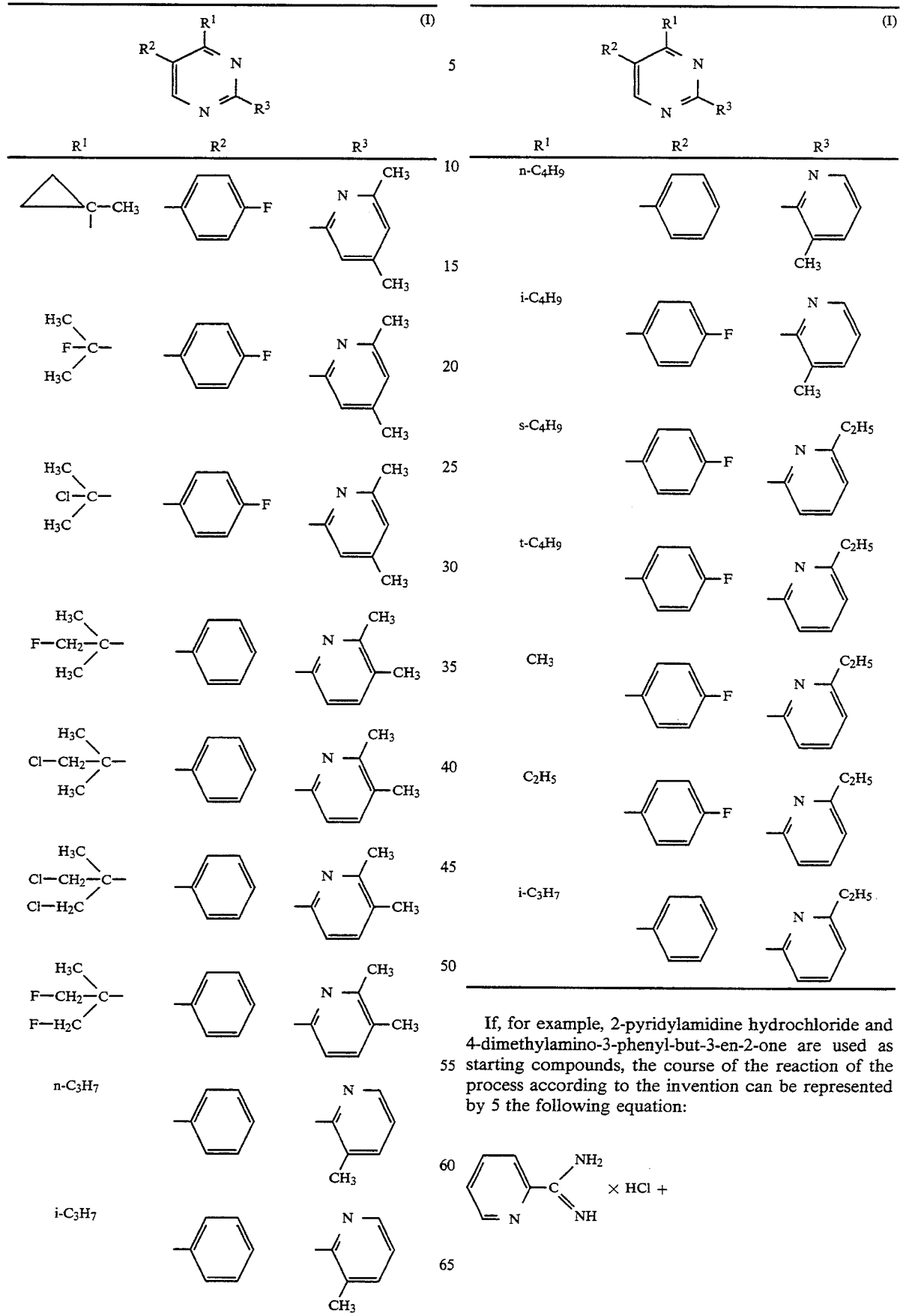
If, for example, 2-pyridylamidine hydrochloride and 4-dimethylamino-3-phenyl-but-3-en-2-one are used as starting compounds, the course of the reaction of the process according to the invention can be represented by the following equation:
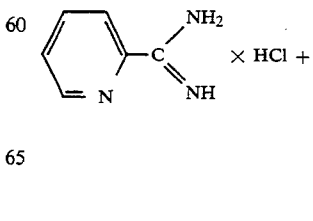

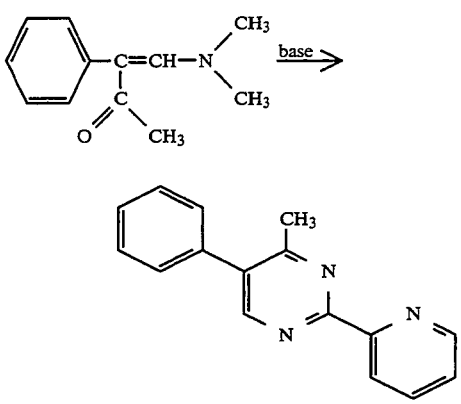

Formula (II) provides a general definition of the pyridylamidine hydrochlorides required as starting compounds for carrying out the process according to the invention. In this formula (II), R³ preferably represents those radicals which have already been mentioned in connection with the description of the compounds of the formula (I) according to the invention as being preferred for this substituent. The pyridylamidine hydrochlorides of the formula (II) are known or can be obtained analogously to known processes (compare, for example, EP 259,139 or EP 270,362).

Formula (III) provides a general definition of the enamino ketones furthermore required as starting substances for carrying out the process according to the invention. In this formula (III), R¹ and R² preferably represent those radicals which have already been mentioned in connection with the description of the compounds of the formula (I) according to the invention as being preferred for these substituents. The enamino ketones of the formula (III) are known or can be obtained analogously to known processes (compare, for example, DE 3,315,797; EP 102,227; DE 3,317,289; EP 61,774; DE 3,012,597; FR 2,477,148; J. Org. Chem. 44, 835–839 [1979]; J. Med. Chem. 21, 623–628 [1978]).

Suitable diluents for carrying out the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethyl formamide, N,N-dimethyl acetamide, N-methylformanilide, N-methylpyrrolidone or hexamethylphosphoric triamide; esters such as methyl acetate or ethyl acetate, or sulphoxides such as dimethyl sulphoxide, or alcohols such as methanol, ethanol as well as n- or i-propanol.

The process according to the invention is preferably carried out in the presence of a suitable reaction auxiliary. Suitable reaction auxiliaries are all customary inorganic and organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium t-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate and also tertiary amines such as trimethylamine, triethylamine, tributylamine, N,N-dimethylaniline, pyridine, N-methylpiperidine, N,N-dimethylaminopyridine, diazabicyclooctane (DABCO) diazabicyclononene (DBN) or diazabicycloundecene (DBU).

When carrying out the process according to the invention, the reaction temperatures can be varied within a substantial range. In general, the process is carried out at temperatures between 20° C. and 140° C., preferably at temperatures between 60° C. and 120° C..

The process according to the invention is customarily carried out under atmospheric pressure. However, it is also possible to carry out the process under increased or reduced pressure. To carry out the process according to the invention, 0.8 to 1.5 mol, preferably 1.0 to 1.2 mol, of enamino ketone of the formula (III) and, if appropriate, 1.0 to 2.0 mol, preferably 1.0 to 1.5 mol, of base used as reaction auxiliary are generally employed per mole of pyridylamidine hydrochloride of the formula (II).

The reaction is carried out and the reaction products are worked up and isolated by known methods (compare, in this context, also the Preparation Examples).

The active compounds according to the invention have a powerful action against pests and can be employed in practice for combating undesired harmful organisms. The active compounds are suitable for use as crop protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed particularly successfully for combating cereal diseases such as, for example, against the causative organism of glume blotch of wheat (*Leptosphaeria nodorum*) or against the causative organism of powdery cereal mildew on wheat or barley (*Erysiphe graminis*) or against diseases in fruit and vegetable growing such as, for example, against the causative organism of powdery mildew of grapevines (*Uncinula necator*) or against the causative organism of apple mildew (*Podosphaera leucotricha*) or against the causative organism of powdery mildew of cucurbits (*Sphaerotheca fuliginea*) or for combating diseases in rice growing such as, for example, against the causative organism of rice blast disease (*Pyricularia oryzae*) or against the causative organism of rice stem blight (*Pellicularia sasakii*). Moreover, the active compounds according to the invention also have a good in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cylcohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seed of the plant can also be treated.

In the treatment of parts of plants, the active compound concentrations in the use forms can be varied within a substantial range. They are, in general, between 1 and 0.0001% by weight, preferably between 0.5 and 0,001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

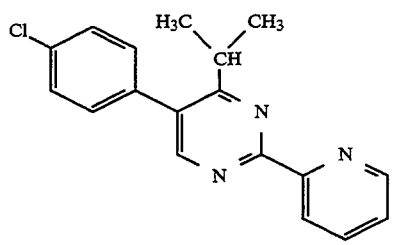

3.2 g (0.02 mol) of pyridine-2-carbamidine hydrochloride (compare, for example, EP 270,362), 5.0 g (0.02 mol) of 1-dimethylamino-2-(4-chlorophenyl)-4-methyl-pent-1-en-3-one and 1.3 g (0,024 mol) of sodium methylate are refluxed for 4 hours in 50 ml of dry methanol, subsequently cooled to room temperature, rendered neutral using glacial acetic acid and concentrated in vacuo, the residue is taken up in t-butyl methyl ether, the mixture is washed with water, dried over sodium sulphate and reconcentrated in vacuo, and the crystalline residue is stirred with diethyl ether, filtered off with suction and dried.

4.0 g (65 % of theory) of 2-(2-pyridyl)-5-(4-chlorophenyl)-4-isopropyl-pyrimidine of melting point 145° C. are obtained.

PREPARATION OF THE STARTING COMPOUND

Example III-1

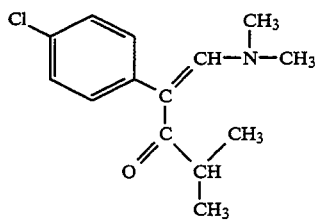

8.5 g (0.041 mol) of 3-methyl-1-(4-chlorophenyl)-butan-2-one (for preparation compare, for example, EP 461,483) and 5.9 g (0,049 mol) of N,N-dimethylformamide dimethyl acetal are refluxed for 16 hours, subsequently cooled to room temperature and evaporated in vacuo, and the crystalline residue is recrystallised from ligroin.

9.0 g ( 87% of theory) of 1-dimethylamino-2-( 4-chlorophenyl)-4-methyl-pent-1-en-3-one of melting point 95 ° C. are obtained.

The following substituted pyridylpyrimidines of the general formula (I)

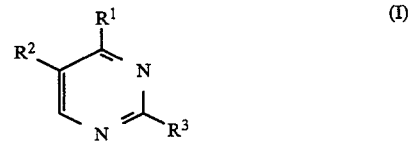

were obtained analogously and following the general preparation instructions.

| Ex. No. | $R^1$ | $R^2$ | $R^3$ | Physical properties |
|---|---|---|---|---|
| 2 | $CH_3-CH_2-CH_2-$ | 2-Cl-phenyl | 2-pyridyl | $^1$H NMR*): 8.7 (s, 1H) |
| 3 | $(CH_3)_2CH-$ | 2-Cl-phenyl | 2-pyridyl | $^1$H NMR*): 8.7 (s, 1H) |
| 4 | $(CH_3)_3C-$ | 2-Cl-phenyl | 2-pyridyl | m.p. 129° C. |
| 5 | cyclopropyl | 4-F-phenyl | 2-pyridyl | m.p. 149° C. |
| 6 | $(CH_3)_2CH-$ | 4-F-phenyl | 2-pyridyl | m.p. 120° C. |

| Ex. No. | R¹ | R² | R³ | Physical properties |
|---|---|---|---|---|
| 7 | 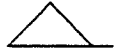 | 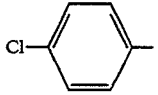 4-Cl-C₆H₄- | 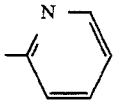 2-pyridyl | m.p. 118° C. |
| 8 | CH₃—CH₂—CH₂— | 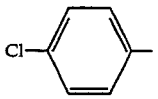 4-Cl-C₆H₄- | 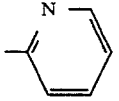 2-pyridyl | m.p. 113° C. |
| 9 | C₂H₅ | 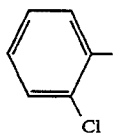 2-Cl-C₆H₄- | 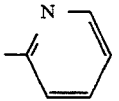 2-pyridyl | m.p. 95° C. |
| 10 | 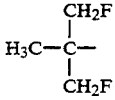 H₃C—C(CH₂F)₂— | 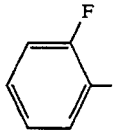 2-F-C₆H₄- | 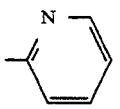 2-pyridyl | ¹H-NMR*): 8,9 (m, 1H) |
| 11 | 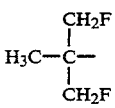 H₃C—C(CH₂F)₂— | 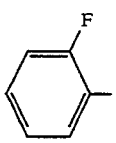 2-F-C₆H₄- | 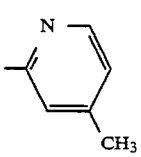 4-CH₃-2-pyridyl | m.p. 143° C. |
| 12 | i-C₃H₇ | 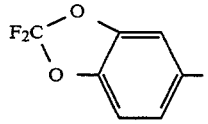 3,4-(OCF₂O)-C₆H₃- | 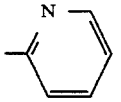 2-pyridyl | m.p. 114° C. |
| 13 |  1-F-cyclopropyl | 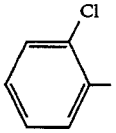 2-Cl-C₆H₄- | 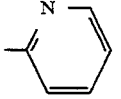 2-pyridyl | m.p. 129° C. |
| 14 | i-C₃H₇ | 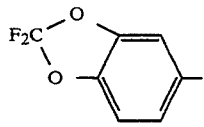 3,4-(OCF₂O)-C₆H₃- | 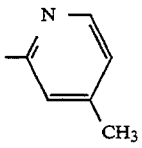 4-CH₃-2-pyridyl | m.p. 124° C. |
| 15 |  cyclopropyl | 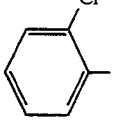 2-Cl-C₆H₄- | 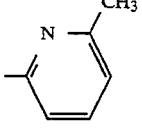 6-CH₃-2-pyridyl | ¹H-NMR*) 8,7 (s, 1H) |
| 16 | i-C₃H₇ | 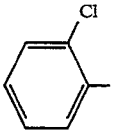 2-Cl-C₆H₄- | 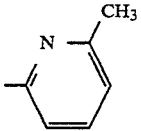 6-CH₃-2-pyridyl | ¹H-NMR*) 8,7 (s, 1H) |
| 17 |  cyclopropyl | 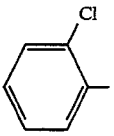 2-Cl-C₆H₄- | 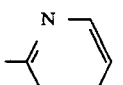 2-pyridyl | m.p. 110° C. |

-continued

| Ex. No. | R¹ | R² | R³ | Physical properties |
|---|---|---|---|---|
| 18 | s-C₄H₉ | 2-Cl-phenyl | 2-pyridyl | ¹H-NMR*): 8,9 (m, 1H) |
| 19 | F—CH₂—C(CH₃)₂— | 2-Cl-phenyl | 2-pyridyl | ¹H-NMR*): 8,6 (s, 1H) |
| 20 | i-C₃H₇ | 2,4-diCl-phenyl | 2-pyridyl | m.p. 157° C. |
| 21 | i-C₄H₉ | 2-Cl-phenyl | 2-pyridyl | ¹H-NMR*): 8,7 (s, 1H) |
| 22 | H₃C—C(CH₂F)₂— | 2-Cl-phenyl | 2-pyridyl | m.p. 108° C. |
| 23 | i-C₃H₇ | 2-F-phenyl | 2-pyridyl | ¹H-NMR*): 8,7 (s, 1H) |
| 24 | i-C₃H₇ | 4-(ClCHF-CF₂-S)-phenyl | 2-pyridyl | m.p. 129° C. |
| 25 | i-C₃H₇ | 4-(F₂CH-S)-phenyl | 2-pyridyl | m.p. 120° C. |

*)The ¹H NMR spectra were recorded in deuterochloroform (CDCl₃) or hexadeutero-dimethyl sulphoxide (DMSO-d₆) with tetramethylsilane (TMS) as the internal standard. The figures indicated are the chemical shift as δ value in ppm.

*) The ¹H NMR spectra were recorded in deuterochloroform (CDCl₃) or hexadeutero-dimethyl sulphoxide ( DMSO-d₆) with tetramethylsilane (TMS) as the internal standard. The figures indicated are the chemical shift as δ value in ppm.

USE EXAMPLES

In the Use Examples which follow, the compounds listed below were employed as comparison substances:

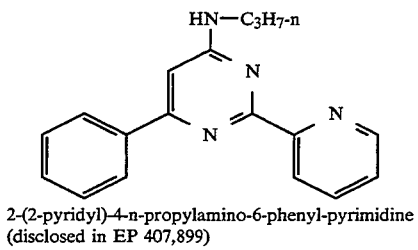

(A)

2-(2-pyridyl)-4-n-propylamino-6-phenyl-pyrimidine (disclosed in EP 407,899)

-continued

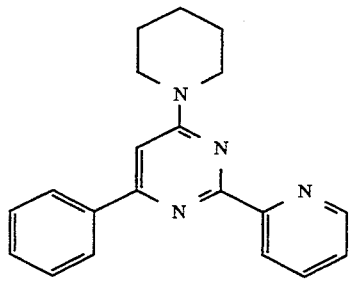

2-(2-pyridyl)-4-(1-piperidinyl)-6-phenyl-pyrimidine
(disclosed in EP 407,899)

(B)

Example A

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of Leptosphaeria nodorum. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after inoculation.

In this test, a clearly superior activity compared with the compound (A) from the prior art is shown, for example, by the compounds of Preparation Examples: 3 and 4.

Example B

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. hordei.*

The plants are placed in a greenhouse at a temperature of about 25° C. and a relative atmospheric humidity of about 80%, in order to promote the development of powdery mildew pustules.

Evaluation is carried out 7 days after the inoculation.

In this test, a clearly superior activity compared with the compound (A) from the prior art is shown, for example, by the compound of Preparation Example 3.

Example C

Erysiphe test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. tritici.*

The plants are placed in a greenhouse at a temperature of about 25° C. and a relative atmospheric humidity of about 80%, in order to promote the development of powdery mildew pustules.

Evaluation is carried out 7 days after the inoculation.

In this test, a clearly superior activity compared with the compound (A) from the prior art is shown, for example, by the compound of Preparation Example 3.

Example D

Uncinula test (grapevines)/protective

Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Uncinula necator.*

The plants are placed in a greenhouse at a temperature of 23° C. to 24° C. and a relative atmospheric humidity of about 75%.

Evaluation is carried out 14 days after the inoculation.

In this test, a clearly superior activity compared with the compound (A) from the prior art is shown, for most of the examples.

Example E

Pyricularia test (rice)/protective

Solvent: 12.5 parts by weight of acetone Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of *Pyricularia oryzae.*

The plants are subsequently placed in a greenhouse at 25° C. and a relative atmospheric humidity of 100%.

Evaluation of the disease level is carried out 4 days after the inoculation.

In this test, a clearly superior activity compared with the compound (B) from the prior art is shown, for example, by the compounds of Preparation Examples: 1, 3, 4, 5, 6, 7 and 8.

Example F

Pellicularia test (rice)

Solvent: 12.5 parts by weight of acetone Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for activity, young rice plants at the 3- to 4leaf stage are sprayed with the preparation of active compound until dripping wet. The plants remain in the greenhouse until they are dry. The plants are subsequently inoculated with *Pellicularia sasakii* and left at 25° C. and a relative atmospheric humidity of 100%.

Evaluation of the disease level is carried out 5 to 8 days after the inoculation.

In this test, a clearly superior activity compared with the compound (B) from the prior art is shown, for example, by the compounds of Preparation Examples: 3 and 4.

We claim:

1. A substituted pyridylpyrimidine of the formula

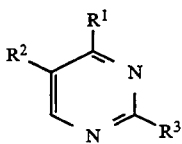

(I)

in which $R^1$ represents straight chain or branched alkyl having 1 to 6 carbon atoms, straight-chain or branched halogenoalkyl having 1 to 6 carbon atoms and 1 to 13 identical or different halogen atoms, or represents cycloalkyl which has 3 to 7 carbon atoms and which is optionally monosubstituted or polysubstituted by identical or different substituents selected from the group consisting of halogen, straight-chain or branched alkyl having 1 to 6 carbon atoms and 1 to 13 identical or different halogen atoms, $R^2$ represents phenyl which is optionally monosubstituted or polysubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy part, straight-chain or branched alkoximinoalkyl having 1 to 4 carbon atoms in the alkoxy part and 1 to 4 carbon atoms in the alkyl part, and phenyl which is optionally monosubstituted or polysubstituted by identical or different substituents selected from the group consisting of halogen and straight-chain or branched alkyl having 1 to 4 carbon atoms, and $R^3$ represents 2-pyridyl, 3-pyridyl or 4-pyridyl, each of which is optionally monosubstituted or polysubstituted by identical or different substituents selected from the group consisting of halogen, cyano, nitro, straight-chain or branched alkyl having 1 to 4 carbon atoms, straight-chain or branched alkoxy having 1 to 4 carbon atoms, straight-chain or branched alkylthio having 1 to 4 carbon atoms, straight-chain or branched halogenoalkyl having 1 to 4 carbon atoms and 1 to 9 identical or different halogen atoms, straight-chain or branched halogenoalkoxy having 1 to 4 carbon atoms and 1 to 9 identical or different halogen atoms, straight-chain or branched halogenoalkylthio having 1 to 4 carbon atoms and 1 to 9 identical or different halogen atoms, straight-chain or branched alkoxycarbonyl having 1 to 4 carbon atoms in the alkoxy part, straight-chain or branched alkoximinoalkyl having 1 to 4 carbon atoms in the alkoxy part and 1 to 4 carbon atoms in the alkyl part, and phenyl which is optionally monosubstituted or polysubstituted by identical or different substituents selected from the group consisting of halogen and straight-chain or branched alkyl having 1 to 4 carbon atoms.

2. A substituted pyridylpyrimidine of the formula (I) according to claim 1, in which $R^1$ represents straight-chain or branched alkyl having 1 to 4 carbon atoms, straight-chain or branched halogenoalkyl having 1 to 4 carbon atoms and 1 to 9 identical or different halogen atoms, or represents cycloalkyl which has 3 to 6 carbon atoms and which is optionally monosubstituted to tetrasubstituted by identical or different substituents selected from the group consisting of halogen, straight-chain or branched alkyl having 1 to 4 carbon atoms or straight-chain or branched halogenoalkyl having 1 to 4 carbon atoms and 1 to 9 identical or different halogen atoms, $R^2$ represents phenyl which is optionally monosubstituted to pentasubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and phenyl which is optionally monosubstituted to trisubstituted by identical or different substituents selected from the group consisting of fluorine, chlorine, bromine, methyl and ethyl, and $R^3$ represents 2-pyridyl or 4-pyridyl, each of which is optionally monosubstituted to tetrasubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and phenyl which is optionally monosubstituted to trisubstituted by identical or different substituents selected from the group consisting of fluorine, chlorine, bromine, methyl and ethyl.

3. A substituted pyridylpyrimidine of the formula (I) according to claim 1, in which $R^1$ represents methyl, ethyl, n- or i-propyl, n-, i-, s- or t-butyl or represents straight-chain or branched halogenoalkyl having 1 to 4 carbon atoms and 1 to 5 identical or different halogen atoms, or represents cyclopropyl, cyclobutyl, cyclopentyl or cyclohexyl, each of which is optionally monosubstituted or disubstituted by identical or different substituents selected from the group consisting of fluorine, chlorine, bromine, methyl, ethyl, n- or i-propyl, chloromethyl or trifluoromethyl, $R^2$ represents phenyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy or trifluoromethylthio and $R^3$ represents 2-pyridyl which is optionally monosubstituted or disubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i- propoxy, n-, i-, s- or t-butoxy, methylthio, ethylthio, trifluoromethyl, trifluoromethoxy and trifluoromethylthio.

4. A compound according to claim 1 of the formula

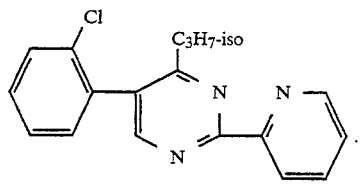

5. A compound according to claim 1 of the formula

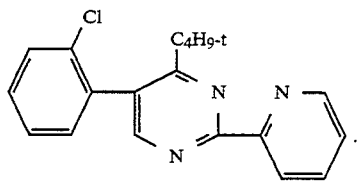

6. A compound according to claim 1 of the formula

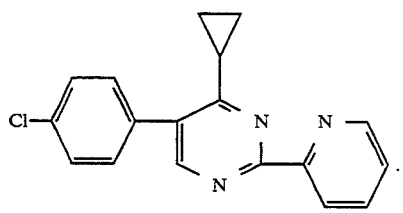

7. A fungicidal composition comprising a fungicidally effective amount of at least one substituted pyridylpyrimidine according to claim 1 and a suitable extender.

8. A method of combating fungi comprising applying to said fungi or an environment thereof a fungicidally effective amount of at least one substituted pyridylpyrimidine according to claim 1.

* * * * *

UNITED STATES PATENT AND TRADEMARK OFFICE
CERTIFICATE OF CORRECTION

PATENT NO. : 5,385,905
DATED : January 31, 1995
INVENTOR(S) : Heinemann, et al.

It is certified that error appears in the above-indentified patent and that said Letters Patent is hereby corrected as shown below:

On the title page item [21], delete Appl. No: "19,989" and substitute --18,989--.

Signed and Sealed this

Twenty-fifth Day of April, 1995

Attest:

BRUCE LEHMAN

Attesting Officer     Commissioner of Patents and Trademarks